United States Patent [19]

Mondadori

[11] 4,409,212

[45] Oct. 11, 1983

[54] METHOD OF PREVENTING AND TREATING CEREBRAL INSUFFICIENCY

[75] Inventor: Cesare Mondadori, Don Mills, Canada

[73] Assignee: Ciba-Geigy Corporation, Ardsley, N.Y.

[21] Appl. No.: 366,792

[22] Filed: Apr. 9, 1982

[30] Foreign Application Priority Data

Apr. 16, 1981 [CH] Switzerland .......................... 2565/81

[51] Int. Cl.$^3$ ............................................. A61K 31/33
[52] U.S. Cl. .................................................. 424/244
[58] Field of Search ........................................ 424/244

[56] References Cited

U.S. PATENT DOCUMENTS 3,637,662  1/1972  Razdan ................................. 424/244
4,076,812  2/1978  Allgeier et al. ...................... 424/244

OTHER PUBLICATIONS

B. M. Kulig and H. Meinardi, Adv. Epileptol, Proc. Congr. Int. League Epilepsy; 13th, 1977 pp. 89-103, C.A. 90, 115155e.

George M. Jacobides, Adv. Epileptol, Proc. Congr. Int. League Epilepsy, 13th, 1977 pp. 114-119, CA 90 11539n.

S. J. Sara and D. Lefevre, Psychopharmacologia 25, 32-40, (1972).

William O. Boggan and Kurt Sclesinger, Behavioral Biology, 12, 127–134, (1974).

*Primary Examiner*—Stanley J. Friedman
*Attorney, Agent, or Firm*—Irving N. Feit; Michael W. Glynn

[57] ABSTRACT

The invention relates to a method of preventing or treating cerebral insufficiency, which method comprises administering to a human being in need of such treatment, orally or rectally, a prophylactic or a therapeutically effective amount of a compound of the general formula I

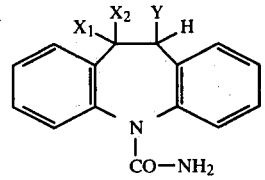

wherein $X_1$ is hydrogen, halogen having an atomic number up to 35, or is cyano, and $X_2$ and Y together are an additional bond, or $X_1$ and $X_2$ together are the oxo radical and Y is hydrogen, or $X_1$ is hydroxy and $X_2$ and Y are hydrogen. Examples of suitable compounds are 10,11-dihyro-10-hydroxy-5H-dibenz[b,f]azepine-5-carboxamide, 10,11-dihydro-10-oxo-5H-dibenz[b,f]azepine-5-carboxamide and, in particular, carbamazepine (5H-dibenz[b,f]azepine-5-carboxamide).

8 Claims, No Drawings

METHOD OF PREVENTING AND TREATING CEREBRAL INSUFFICIENCY

The present invention relates to a method of preventing and treating cerebal insufficiently, in particular impaired memory conditions, as well as to pharmaceutical compositions for use in said method and to the production thereof.

A nootropic drug which has attained great medicinal importance in the treatment of e.g. the organocerebral psychosyndrome and sequels of cerebral traumas or apoplexy, is piracetam (BAN, DCF, chemical name: 2-oxo-1-pyrrolidineacetamide). Derivatives and further related compounds of piracetam are in the clinical testing stage. One of the most conspicuous properties of nootropic drugs of the piracetam type within the scope of the animal tests customarily employed in screening is its ability to protect freshly obtained information from the amnesiogenous action of cerebral electroshock. Piracetam, and all derivatives thereof which have so far been clinically tested, have this ability.

Surprisingly, it has now been found that carbamazepine (BAN etc., chemical name: 5H-dibenz[b,f]azepine-5-carboxamide) and related compounds, when administered both in doses which effect 100% prevention of the convulsions provoked by electroshock ($ED_{100}$) and in lower doses, e.g. corresponding to $ED_{50}$ or even below, are able to prevent the amnesiogenous action of electroshock to at least the same or to an even greater degree than piracetam. An advantageous ratio of equivalent doses of e.g. carbamazepine to piracetam of about 1 to 10 results from these tests, whereas the ratio of carbamazepine and piracetam employed so far in practice, where carbamazepine is used for the treatment of epilepsy or trigeminal neuralgia, is about 1 to 4 in oral administration.

The findings referred to above can be established in the following one-step learning test with mice.

The test equipment consists of a large box (35×20×10 cm) which is joined by means of a sliding door to a small box (10×10×18 cm). The small box is brightly lit from above by a 100 watt lamp, whereas the large box is dark. The floor of both compartments consists or an electrifiable grating.

For treating, the mice are put individually into the brightly lit small box. As mice have an instinctive preference for the dark, they usually go into the dark compartment within 30 seconds. As soon as they have gone into this dark with all legs compartment, the sliding door is closed and a shock (1 mA, 5 seconds) is administered to the feet of the mice. The animals are then immediately taken out of the testing unit.

To test the learning performance (retest), the mice are once more put individually into the lit compartment and the latency until they are all in the dark is measured. Most of the animals will now normally remain in the lit compartment over the entire observation time of 150 seconds.

The learning performance is substantially annulled, i.e. the memory of the shock to the fact is at least partially extinguished, if, as amnesiogenous treatment, a brief electroshock treatment follows directly on the shock to the feet administered in the training run. Parameters of the electroshock: 50 mA, 0.4 sec., 50 Hz, 0.6 msec. pulse width.

For testing and comparing their protective action on the amnesiogenous action of the electroshock, the test substances are each administered intraperitoneally 30 minutes before training in the form of a suspension in methocel, and the animals are subjected immediately after training to the electroshock treatment. The degree of the learning performance still retained is measured from the residence time in the lit box and compared with that of the other test substances as well as of control animals to which methocel only has been administered, and training without and training with subsequent electroshock treatment. Using 10 mice per dose and doses of 1, 3, 10, 30 and 100 mg/kg, the following doses still significantly effective according to the Mann-Whitney U-test, i.e. $DE_{min}$, were determined: piracetam 100 mg/kg, carbamazepine 10 mg/kg, 10,11-dihydro-10-oxo-5H-dibenz[b,f]azepine-5-carboxamide 10 mg/kg, 10,11-dihydro-10-hydroxy-5H-dibenz[b,f]azepine-5-carboxamide 10 mg/kg, 10-chloro-5H-dibenz[b,f]azepine-5-carboxamide 10 mg/kg, 10-cyano-5H-dibenz[b,f]azepine-5-carboxamide 1 mg/kg.

The following literature on similar assays may be cited by way of example: S. J. Sara and D. Lefevre, Psychopharmacologia 25, 32–40 (1972), Hypoxia-induced amnesia in one-trial learning and pharmacological protection by piracetam; Boggan, W. O and Schlesinger, K., in Behavioural Biology 12, 127–134 (1974).

With anticonvulsive and antiepileptic compounds of different chemical constitution it was not possible to detect any diminution of the amnesiogenous action of the electroshock in the same experimental method on administration of the dose which effects 100% prevention of convulsion ($ED_{100}$), so that it may be assumed that the determined action of carbamazepine and related compounds is not a general consequence of the prevention of convulsion, but resides in a specific property of the group of compounds defined by the general formula I.

Accordingly, the present invention relates to a method of preventing or treating cerebral insufficiently, in particular impaired memory conditions of different provenance such as senile dementia, multi-infarction dmentia or Alzheimer's dementia, and also sequels of cerebral traumas or apoplexy, which method comprises administering to a human being in need of such treatment, orally or rectally, a prophylactic or a therapeutically effective amount of a compound of the general formula I

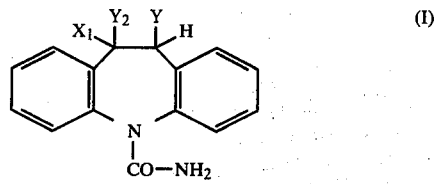

wherein $X_1$ is hydrogen, halogen having an atomic number up to 35, or is cyano, and $X_2$ and Y together are an additional bond, or $X_1$ and $X_2$ together are the oxo radical and Y is hydrogen, or $X_1$ is hydroxy and $X_2$ and Y are hydrogen. Preferred compounds are those in which $X_1$ is hydrogen, chlorine or cyano, and $X_2$ and Y together are an additional bond, or $X_1$, $X_2$ and Y have the further meanings indicated above, e.g. 10,11-dihydro-10-hydroxy-5H-dibenz[b,f]azepine-5-carboxamide, preferably 10,11-dihydro-10-oxo-5H-dibenz[b,f]azepine-5-carboxamide and, most preferably, carbamazepine (5H-dibenz[b,f]azepine-5-carboxamide). The dosage depends on the nature of the disorder, the individual condition, the age and weight of the patient, and on the duration of the treatment, and is, in particular, in the range from about 2 to 17 mg/kg per day or from about 150 to 1200 mg per day for an adult having a normal body weight of about 70 kg. Based on the individual compounds of the general formula I, the daily dose is normally only about one third to one half of the doses necessary for the treatment of epilepsy or trigeminal neuralgia, whereby the compounds administered in the method of the invention are well to very well tolerated.

Pharmaceutical compositions for use in the present invention may be in a single dosage unit form, i.e. dosage unit formulations for oral administration, such as tablets, dragées or capsules, or for rectal administration, such as suppositories, or they may be formulations for oral administration which are not in single dosage form, such as syrups. Dosage unit formulations contain a compound of the general formula I in an amount suitable for ingestion of the above mentioned daily dose by taking preferably one or two dosage unit formulations once or more than once, preferably at most three times, most preferably two times, i.e. the entire daily dose or a third or, in particular, half the daily dose, or half, one sixth or one quarter, corresponding to about 25 to 600 mg, preferably about 50 to 300 mg. Instead of administering one single compound of the general formula I, several compounds may be administered together, in which case the total doses and amounts likewise remain within the range indicated for the individual compounds.

Divisible dosage unit formulations, such as tablets with breaking notch, and those with delayed release of active ingredient, may also contain higher amounts of active ingredient, whereas dosage unit formulations for administration to children may also contain correspondingly lower amounts.

Formulations for oral administration not in single dosage unit form, such as syrups, contain amounts of active ingredient corresponding to those of a single dosage unit formulations, in suitable amounts or volume units of e.g. 2.5, 5 or 10 ml.

The pharmaceutical compositions which may be used in the method of this invention contain one or more compounds of the general formula I, preferably together with inorganic or organic, solid or liquid, pharmaceutically acceptable carriers which are suitable for enteral, e.g. oral, administration. Tablets or dragées cores are prepared by combining the active ingredients e.g. with solid pulverulent carriers such as lactose, dextrose, saccharose, mannitol, sorbitol, cellulose and/or glycine, optionally with the addition of glidants and lubricants, e.g. silica, talcum, stearic acid or salts thereof, such as magnesium or calcium stearate, and/or polyethylene glycol, optionally with the addition of binders, e.g. magnesium aluminium silicate, starches such as corn, wheat, rice or arrow root starch, gelatin, tragacanth, methyl cellulose, sodium carboxymethylcellulose and/or polyvinylpyrrolidone, and, if desired, disintegrators, e.g starches, agar, alginic acid or salts thereof, such as sodium alginate, and/or effervescent mixtures, or adsorption agents, colorants, flavouring matters and sweeteners. Dragée cores are coated e.g. with concentrated sugar solutions which may additionally contain e.g. gum arabic, talcum and/or titanium dioxide, or provided with a shellac coating which is dissolved in readily volatile organic solvents or solvent mixtures. Colorants can be added to the coatings, for example to identify different doses of active ingredient.

Further dosage unit forms for oral administration are dry-filled capsules made from gelatin and soft sealed capsules made from gelatin and a plasticiser such as glycerol. The dry-filled capsules preferably contain a granular formulation of the active ingredient, e.g. in admixture with fillers such as corn starch, and/or with lubricants such as talcum or magnesium stearate, and, if desired, with stabilisers, e.g. ascorbic acid. In soft capsules the active ingredient is preferably dissolved or suspended in suitable liquids, e.g. liquid polyethylene glycols, to which stabilisers can also be added.

Suitable formulations which are not in dosage unit form are, in particular, syrups prepared in conventional manner which preferably contain a suspension of the compound of the general formula I.

The pharmaceutical compositions can be sterilised and/or contain adjuvants, e.g. preservatives, stabilisers, wetting agents and/or emulsifiers, solubilisers, salts for regulating the osmotic pressure, and/or buffers. The pharmaceutical compositions of the invention which, if desired, can contain further pharmacologically active substances, are prepared in a manner known per se, for example by conventional mixing, granulating, confectioning or dissolving methods, and they contain from about 10% to 100%, preferably from about 20% to 80%, of one or more compounds of the general formula I.

EXAMPLE 1

Tablets each containing 50 g of 5H-dibenz[b,f]-azepine-5-carboxamide can be prepared as follows:

| Composition (1000 tablets) | |
|---|---|
| 5H—dibenz[b,f]azepine-5-carboxamide | 50.0 g |
| lactose | 500.0 g |
| potato starch | 352.0 g |
| gelatin | 8.0 g |
| talcum | 60.0 g |
| magnesium stearate | 10.0 g |
| highly disperse silica | 20.0 g |
| ethanol | q.s. |

The active ingredient is mixed with the lactose and 292 g of potato starch and the mixture is moistened with an alcoholic solution of the gelatin and granulated through a sieve. After drying, the remainder of the potato starch, the talcum, magnesium stearate and the highly disperse silica are admixed and the mixture is compressed to tablets each weighing 145.0 mg and containing the indicated amount of active ingredient. If desired, these tablets can be provided with a breaking notch for a finer adjustment of the dose.

EXAMPLE 2

Shellac coated tablets each containing 100 mg of 5H-dibenz[b,f]azepine-5-carboxamide can be prepared as follows:

| Composition (for 1000 tablets) | |
|---|---|
| 5H—dibenz[b,f]azepine-5-carboxamide | 100.00 g |
| lactose | 100.00 g |
| corn starch | 70.00 g |
| talcum | 8.50 g |
| calcium stearate | 1.50 g |
| hydroxypropylmethylcellulose | 2.36 g |
| shellac | 0.64 g |
| water | q.s. |

| Composition (for 1000 tablets) | |
|---|---|
| methylene chloride | q.s. |

The active ingredient, the lactose, and 40 g of the corn starch are mixed and the mixture is moistened with a starch paste prepared from 15 g of corn starch and water (with heating) and granulated. The granulate is dried and the remainder of the corn starch, the talc and the calcium stearate are added to and mixed with the granulate. The mixture is compressed to tablets weighing 280 g and these are then coated with a solution of the hydroxypropylmethyl-cellulose and the shellac in methylene chloride. Final weight of the coated tablets: 282 mg.

In addition to carbamazepine (5H-dibenz[b,f]-azepine-5-carboxamide), compounds of the general formula I generally suitable for use in the foregoing Examples are e.g. 10-oxo-10,11-dihydro-5H-dibenz[b,f]azepine-5-carboxamide (q.v. U.S. Pat. No. 3,643,775) and 10-hydroxy-10,11-dihydro-5H-dibenz[b,f]azepine-5-carboxamide (q.v. U.S. Pat. No. 3,637,667), as well as 10-fluoro-, 10-chloro- and 10-bromo-5H-dibenz[b,f]azepine-5-carboxamide (q.v. U.S. Pat. No. 4,076,812) and 10-cyano-5H-dibenz[b,f]azepine-5-carboxamide (q.v. European patent application 11.603).

What is claimed is:

1. A method of preventing or treating imparied memory conditions comprising administering to a human being in need of such treatment, orally or rectally, a prophylactic or a therapeutically effective amount of a compound of the general formula

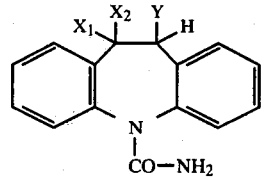

wherein $X_1$ is hydrogen, halogen having an atomic number up to 35, or is cyano, and $X_2$ and Y together are an additional bond, or $X_1$ and $X_2$ together are the oxo radical and Y is hydrogen, or $X_1$ is hydroxy and $X_2$ and Y are hydrogen.

2. The method according to claim 1 wherein the impaired memory conditions comprise senile dementia, multi-infarction dementia, or Alzheimer's dementia.

3. A method according to claim 1, which comprises administration of a compound of the general formula I, wherein $X_1$ is hydrogen, chlorine or cyano, and $X_2$ and Y together are an additional bond, or $X_1$ and $X_2$ together are the oxo radical and Y is hydrogen, or $X_1$ is hydroxy and $X_2$ and Y are hydrogen.

4. A method according to claim 1, which comprises administration of 5H-dibenz[b,f]azepine-5-carboxamide.

5. A method according to claim 1, which comprises administration of 10,11-dihydro-10-oxo-5H-dibenz[b,f]-azepine-5-carboxamide.

6. A method according to claim 1, which comprises administration of 10,11-dihydro-10-hydroxy-5H-dibenz[b,f]-azepine-5-carboxamide.

7. A method according to claim 1, which comprises administration of a compound of the general formula I in an amount from 2 to 17 mg/kg per day.

8. A method according to claim 18, which comprises administration of a compound of the general formula I to an adult person of normal weight in an amount from about 150 to 1200 mg per day.

* * * * *

UNITED STATES PATENT AND TRADEMARK OFFICE
CERTIFICATE OF CORRECTION

PATENT NO. : 4,409,212
DATED : Oct. 11, 1983
INVENTOR(S) : Cesare Mondadori

It is certified that error appears in the above-identified patent and that said Letters Patent is hereby corrected as shown below:

In Column 5:

Claim 1; line 1 should read:
--A method of preventing or treating impaired mem-.--

In Column 6:

Claim 8; line 1 should read:
--A method according to claim 1 which comprises--

Signed and Sealed this

Twentieth Day of June, 1989

Attest:

DONALD J. QUIGG

*Attesting Officer*   *Commissioner of Patents and Trademarks*